United States Patent
Baldwin

(10) Patent No.: US 11,406,330 B1
(45) Date of Patent: Aug. 9, 2022

(54) SYSTEM TO OPTICALLY DETERMINE BLOOD PRESSURE

(71) Applicant: AMAZON TECHNOLOGIES, INC., Seattle, WA (US)

(72) Inventor: Leo Benedict Baldwin, Seattle, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 353 days.

(21) Appl. No.: 16/142,840

(22) Filed: Sep. 26, 2018

(51) Int. Cl.
*A61B 5/00* (2006.01)
*A61B 5/0205* (2006.01)
(Continued)

(52) U.S. Cl.
CPC .......... *A61B 5/7278* (2013.01); *A61B 5/0077* (2013.01); *A61B 5/02055* (2013.01);
(Continued)

(58) Field of Classification Search
CPC .. A61B 5/00; A61B 5/02; A61B 5/021; A61B 5/7278; A61B 5/0077; A61B 5/02055; A61B 5/1032; A61B 5/1075; A61B 5/1079; A61B 5/489; A61B 5/681; A61B 5/02255; A61B 5/02438; A61B 5/14532; A61B 5/14551; A61B 2560/0223; A61B 2560/0252; A61B 2562/0219; A61B 2576/02; G06T 7/13; G06T 2207/10048; G06T 2207/30101; H04N 5/2354
See application file for complete search history.

(56) References Cited

U.S. PATENT DOCUMENTS

2007/0276260 A1* 11/2007 Hammer ............ A61B 5/02007
600/479
2014/0294235 A1* 10/2014 Ishida .................. G06K 9/0061
382/103
(Continued)

FOREIGN PATENT DOCUMENTS

JP  1176216 A  3/1999
JP  2010508056 A  3/2010
(Continued)

OTHER PUBLICATIONS

OmniVision, "Low-Power, Ultra-Compact Global Shutter Sensor for Computer Vision Applications", Version 13, Sep. 2017, Retrieved from the Internet: https://www.ovt.com/download/sensorpdf/147/OmniVision_OV6211.pdf.

*Primary Examiner* — Yi-Shan Yang
*Assistant Examiner* — Alexei Bykhovski
(74) *Attorney, Agent, or Firm* — Lindauer Law, PLLC

(57) ABSTRACT

A camera sensitive to near infrared light is placed proximate to the skin of a user and the area illuminated by one or more infrared light sources. A set of images of one or more blood vessels is obtained at successive times. The images are processed to determine a change in size of the vessel(s) from one time to another, corresponding to expansion and contraction of the vessels responsive to contraction of the user's heart. This change may be used to determine pulse rate, elasticity of the vessel, blood pressure, or other data about the user's physiological status. The data may be used to assess health status at a particular time, determine health trends for the user, and so forth.

21 Claims, 7 Drawing Sheets

(51) Int. Cl.
*A61B 5/103* (2006.01)
*A61B 5/107* (2006.01)
*G06T 7/13* (2017.01)
*H04N 5/235* (2006.01)
*A61B 5/0225* (2006.01)
*A61B 5/024* (2006.01)
*A61B 5/145* (2006.01)
*A61B 5/1455* (2006.01)

(52) U.S. Cl.
CPC .......... *A61B 5/1032* (2013.01); *A61B 5/1075* (2013.01); *A61B 5/1079* (2013.01); *A61B 5/489* (2013.01); *A61B 5/681* (2013.01); *G06T 7/13* (2017.01); *H04N 5/2354* (2013.01); *A61B 5/02255* (2013.01); *A61B 5/02438* (2013.01); *A61B 5/14532* (2013.01); *A61B 5/14551* (2013.01); *A61B 2560/0223* (2013.01); *A61B 2560/0252* (2013.01); *A61B 2562/0219* (2013.01); *A61B 2576/02* (2013.01); *G06T 2207/10048* (2013.01); *G06T 2207/30101* (2013.01)

(56) References Cited

U.S. PATENT DOCUMENTS

| | | | |
|---|---|---|---|
| 2016/0022210 A1 | 1/2016 | Nuovo et al. | |
| 2016/0073905 A1* | 3/2016 | Murai | A61B 5/021 600/484 |
| 2017/0112577 A1* | 4/2017 | Bonutti | A61B 90/361 |
| 2018/0000511 A1* | 1/2018 | Fujie | A61B 17/3403 |
| 2018/0132797 A1* | 5/2018 | Draeger | A61B 5/1072 |
| 2018/0352159 A1* | 12/2018 | Kim | H04N 13/239 |
| 2019/0038151 A1* | 2/2019 | Lee | A61B 5/6898 |
| 2019/0057189 A1* | 2/2019 | Frederickson | G08B 21/0446 |

FOREIGN PATENT DOCUMENTS

| | | |
|---|---|---|
| JP | 2018114037 A | 7/2018 |
| KR | 20110022132 A | 3/2011 |
| WO | 2018030665 A1 | 2/2018 |

\* cited by examiner

SYSTEM TO OPTICALLY DETERMINE BLOOD PRESSURE

BACKGROUND

Physiological data may be used to help a user manage their health, make more informed decisions, and improve the quality of their life. For example, physiological data such as systolic and diastolic blood pressure readings may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
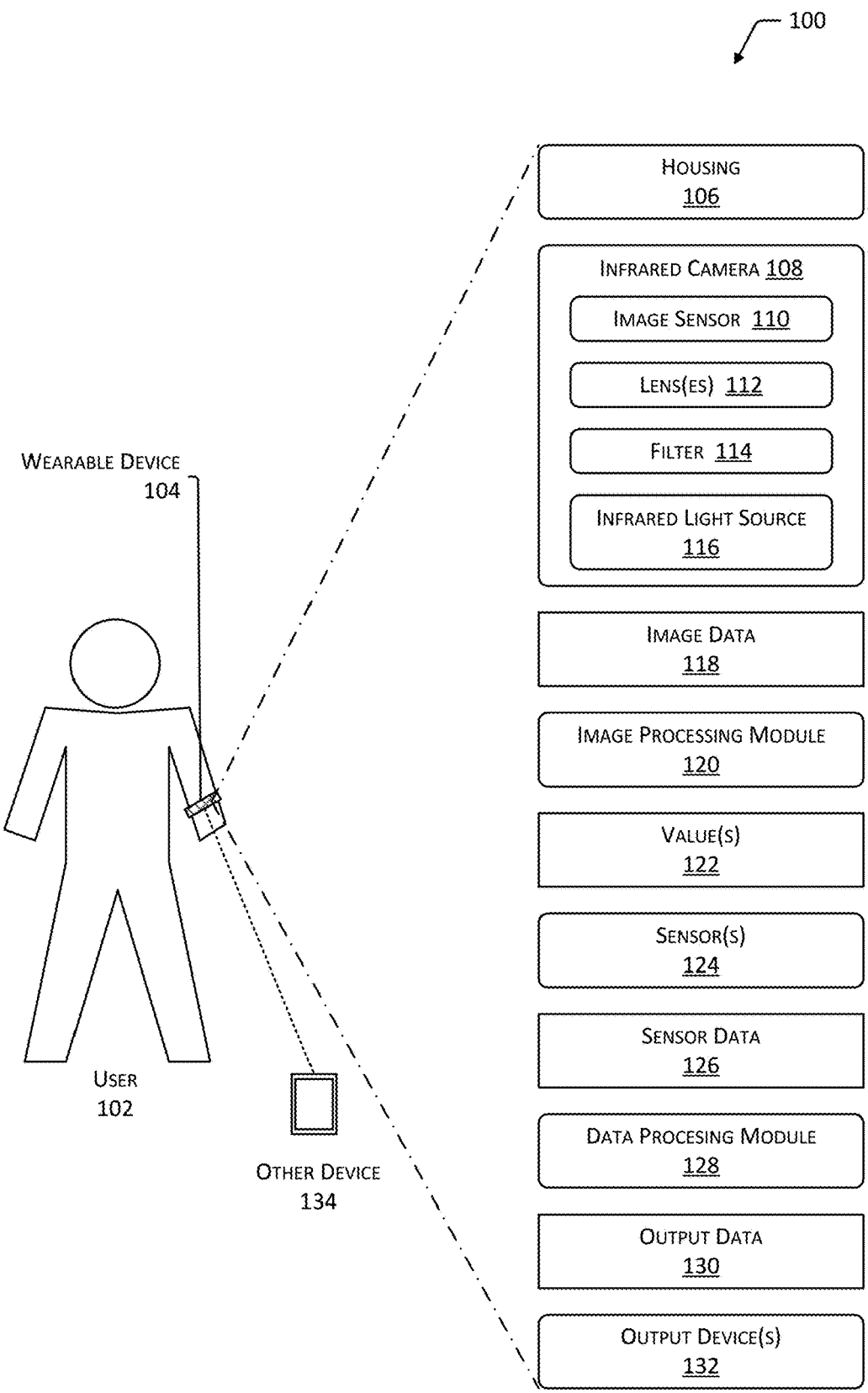
FIG. 1 is an illustrative system that may include a user, a wearable device with an infrared camera to obtain images of a portion of a user to determine one or more values, such as blood pressure, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

Information about vital signs of a user may be used to inform the user as to their physical condition. These vital signs may include blood pressure, pulse or heart rate, body temperature, oxygen saturation of blood, and so forth. Information about one or more of these vital signs at a particular time, about trends over time, and so forth may help a user to regulate their activity, provide feedback to make healthy lifestyle changes, and so forth. For example, if at a particular time a user's blood pressure has exceeded a threshold value, it may be worthwhile for the user to engage in a calming routine, physically rest, and so forth to reduce their blood pressure.

Humans have a circulatory system made up of a network of blood vessels in which blood is pumped by the heart. The blood supplies oxygen and nutrients to the body and removes waste products such as carbon dioxide. The blood vessels include arteries and veins. Arteries supply oxygen-rich blood from the heart while veins carry oxygen-depleted blood back to the heart. During a contraction of the heart, the pressure within the arteries temporarily increases as the blood is pushed through the arteries. The walls of a healthy blood vessel are elastic, and under the pressure increase in the blood produced by the contraction of the heart, they expand or dilate, increasing in diameter. As the contraction of the heart concludes, the elastic walls of the vessel return back to their earlier state with a narrower diameter.

Heart rate or pulse indicates the frequency at which the heart is contracting per unit time, such as 60 beats per minute (bpm). Blood pressure may refer to pressure of larger arteries and may comprise two values: a systolic pressure and a diastolic pressure. The systolic pressure is indicative of the maximum pressure measured in an artery during the contraction of the heart. The diastolic pressure indicates the minimum pressure present in the artery between contractions.

The blood pressure of a user normally changes due to various stimuli and conditions. For example, blood pressure when a user is standing is generally greater than when the user is laying down. Blood pressure may increase when a user encounters a stressful situation and may drop when the user relaxes.

Various long-term physical conditions result in changes to blood pressure. For example, hypertension is when the blood pressure of a user is greater than a threshold value. Hypertension, especially over longer periods of time, may be associated with damage to one or more organs. As a result, it is useful to be able to monitor blood pressure at particular times, as well as monitoring over longer periods of time to determine trends that may be indicative of health concerns.

Traditional techniques for measuring blood pressure are cumbersome. One such technique is use of a sphygmomanometer in which an inflatable cuff is placed around a limb and used to apply a varying level of pressure to an artery while listening for the sound of blood moving through the artery. For example, a cuff is placed above the elbow of a user's arm and used to apply pressure to the brachial artery while a stethoscope is used to listen. Electronic sphygmomanometers are also available that automatically determine the blood pressure. While accurate when properly used and calibrated, sphygmomanometers whether manual or automatic are bulky and involve the use of a cuff. This limits the use of sphygmomanometers to situations where the bulky device can be carried or stored. Additionally, some users may find the use of an inflatable cuff uncomfortable.

Another technique for the measurement of blood pressure is more invasive. A catheter may be inserted into a blood vessel and used to directly measure blood pressure. However, such a technique is uncomfortable for the user, expensive, requires professional skill to use, and may involve the potential for adverse events.

Described in this disclosure is a system that is designed to non-invasively acquire values about blood vessels. These values may then be used to determine information such as the blood pressure of the user. A device including an infrared (IR) camera sensitive to near infrared (IR) light with a wavelength of between 700 nanometers (nm) and 1000 nm and infrared illuminators is placed proximate to a user's skin. For example, the IR camera and IR light emitting diodes (LED) may be included in a wristband. The IR camera includes a wide-angle lens, allowing it to acquire an image from a relatively large area. Because the IR light passes through the skin and tissues of the user, the resulting image data may depict one or more blood vessels. For example, the image data may comprise video obtained at 30 frames per second (FPS) of the blood vessels during several beats of the user's heart.

The image data is processed to determine the presence of the blood vessels. For example, edge detection algorithms may be used to find the walls of the arteries and veins that are depicted in the images. In some implementations features in the images that are considered to be blood vessels may be required to have a minimum size. The image data may be processed to determine images and areas of interest within those images that depict the blood vessels. In some implementations a determination may be made as to whether a vessel is an artery or a vein. For example, a vessel that exhibits a greatest relative percentage increase in distance from one wall to another from minimum to maximum may be designated as an artery.

The image data is processed to determine one or more values. These values may include a distance indicative of a diameter extending from a first wall of the blood vessel to a second wall that is opposite the first wall, a percentage change in diameter from a minimum diameter to a maximum diameter, or a ratio of a first diameter of a first blood vessel to a second diameter of a second blood vessel at a particular time. The values may include time-based data, such as a rate of change in diameter over time.

In some implementations the values may be used to determine information such as blood pressure. For example, the system may be used to acquire values while an external sphygmomanometer is used to generate sphygmomanometric data indicative of blood pressure. Several different readings from both the system and from the sphygmomanometer may be acquired at different times, and sphygmomanometric correspondence data may be determined. For example, the sphygmomanometric correspondence data may provide a relationship between particular distances from one blood vessel wall to another and one or more of systolic or diastolic blood pressure. Later, the sphygmomanometric correspondence data may be used to produce blood pressure data based on the image data obtained by the IR camera.

The system as described in this disclosure may be incorporated into at least a portion of a wearable device, portable device, or a fixed device. For example, a wearable device may include the IR camera, illuminators, and a computing device that allows for determination of one or more values. These values may then be used to determine the blood pressure data based on the image data. In another example, the wearable device may send at least a portion of the image data to another device, such as a smartphone, tablet computer, laptop, server, and so forth. The image data may then be processed to determine one or more values.

By using the system described in this disclosure, a user is able to obtain information about their health. This information may be used to help them manage their activities to maximize the quality of their health.

Illustrative System

FIG. 1 is an illustrative system 100 that may include a user 102 and a wearable device 104 that is used to determine one or more values associated with a physiological state of the user, according to one implementation. In some implementations, these values may be used to determine one or more vital signs of the user, such as blood pressure.

The user 102 may have one or more wearable devices 104 on or about their person. The wearable device 104 may be implemented in various physical form factors including, but not limited to, the following: hats, headbands, necklaces, pendants, brooches, torcs, armlets, brassards, bracelets, wristbands, belts, anklets, and so forth. In this illustration, the wearable device 104 is depicted as a wristband. In some implementations the user 102 may wear multiple wearable devices 104.

The wearable device 104 includes a housing 106. The housing 106 comprises one or more structures that support an infrared (IR) camera 108. The IR camera 108 comprises an image sensor 110 that is sensitive to near infrared (IR) light. The near IR light may have a wavelength of between 700 nanometers (nm) and 1000 nm. The image sensor 110 may comprise charge coupled devices (CCD), complementary metal oxide semiconductor (CMOS) devices, microbolometers, quantum-dot imagers, and so forth.

The IR camera 108 may include one or more lenses 112. The lenses 112 may include a wide-angle lens 112 with a field of view (FOV) that is greater than or equal to 90 degrees measured diagonally across opposite corners. When the wearable device 104 is in use, the lens(es) 112 are proximate to the skin of the user 102. For example, if the wearable device 104 is a wristband, the lens 112 may be proximate to the interior surface of the wristband.

A filter 114 may be included in an optical path of the infrared camera 108 that transmits a first range of infrared wavelengths and attenuates wavelengths outside of that range. For example, if the image sensor 110 is sensitive to visible and IR light, the filter 114 may be used to attenuate the visible light and operate as a band pass filter in which the IR light reaches the image sensor 110.

The infrared camera 108 may include, or operate in conjunction with, one or more infrared light sources 116. For example, the infrared light source 116 may comprise a light emitting diode that emits IR light at a wavelength that is detectable by the image sensor 110. The passband spectra of filter 114 may be designed to align with the emission spectra of infrared light source 116. The infrared camera 108 is discussed in more detail below with regard to FIG. 4.

During operation, the infrared light source 116 is activated, and the infrared camera 108 obtains image data 118 comprising a first set of images. For example, the infrared camera 108 may generate image data 118 comprising video of a portion of the user's 102 arm.

The image data 118 is processed by an image processing module 120 to determine one or more values 122. The image processing module 120 may process the first set of images and determine a second set of images that depict at least one blood vessel. In one implementation, the image processing module 120 may use an edge detection algorithm to determine the edges of blood vessels depicted in the image data 118. For example, a Canny edge detector may be used to determine edges depicted in the image data 118. The image processing module 120 may disregard discontinuous edges that have a length that is below a threshold value. In other implementations, other techniques may be used to determine the blood vessels in the image data 118. For example, a neural network may be trained to process image data 118 and determine a portion of an image that is likely to contain a blood vessel.

The image processing module 120 generates values 122 that are representative of one or more attributes of the blood vessels as they appear in the image data 118 at one or more times. The values 122 may include one or more of a distance indicative of a chord or diameter extending from a first wall of a particular blood vessel to a second wall that is opposite the first wall, a percentage change in diameter from a minimum diameter to a maximum diameter, or a ratio of a first diameter of a first blood vessel to a second diameter of a second blood vessel at a particular time. The values 122 may include time-based data, such as a rate of change in diameter over time.

One or more of the modules in the image processing module 120 may implement, at least in part, one or more of the following tools or techniques available in the OpenCV library as developed by Intel Corporation of Santa Clara, Calif., USA; Willow Garage of Menlo Park, Calif., USA; and Itseez of Nizhny Novgorod, Russia. In another implementation, functions available in the OKAO machine vision library as promulgated by Omron Corporation of Kyoto, Japan, may be used to process sensor data 126. In still another implementation, functions such as those in the Machine Vision Toolbox for Matlab (MVTB) available using MATLAB as developed by MathWorks, Inc. of Natick, Mass., USA, may be utilized. Other libraries, functions, or tools may be utilized as well.

The devices described herein, such as the wearable device 104, may include one or more sensors 124 configured to generate sensor data 126. For example, the wearable device 104 may comprise a motion sensor, such as an accelerometer, gyroscope, or both. In some implementations, data obtained from the one or more sensors 124 may be used to trigger acquisition or processing of the image data 118. For example, if the motion sensor(s) produces sensor data 126 indicative of movement of the wearable device 104 that exceeds a threshold value, the infrared camera 108 may be operated to produce image data 118. Data from the accelerometer, gyroscope, or both may be used to categorize the blood pressure measurements as "resting" or "active". The sensors 124 are discussed in more detail with regard to FIG. 2. The computing device is discussed in more detail below with regard to FIG. 3.

A data processing module 128 may use the one or more values 122 produced by the image processing module 120 to generate output data 130. For example, based at least in part on a distance between walls of a blood vessel, output data 130 may be determined that is indicative of blood pressure of the user 102.

In some implementations, the data processing module 128 may utilize one or more values 122 associated with image data 118 obtained by other wearable devices 104. For example, the user 102 may be wearing a wearable device 104(1) on a wrist and another wearable device 104(2) near an ankle. The values 122 obtained by the respective device may be used to determine one or more metabolic conditions. For example, the time interval between an increase in systolic pressure in the arm and an increase in systolic pressure near the ankle may be measured and used to characterize function of the user's 102 cardiovascular system.

The wearable device 104 may include one or more output devices 132. The output devices 132 may provide output that may be perceived by the user 102. For example, the data processing module 128 may determine that the distance between the walls of the blood vessel exceeds a threshold value, and may generate instructions that cause the output devices 132 to emit an audible, visual, or haptic output.

The wearable device 104 may be in communication with one or more other devices 134. For example, the other devices 134 may include a smart phone, tablet computer, electronic book (e-book) reader device, set-top box, media player, gaming console, personal computer, server, electronic sphygmomanometer, internet enabled device, voice activated device, smart-home device, and so forth.

Figure 2:
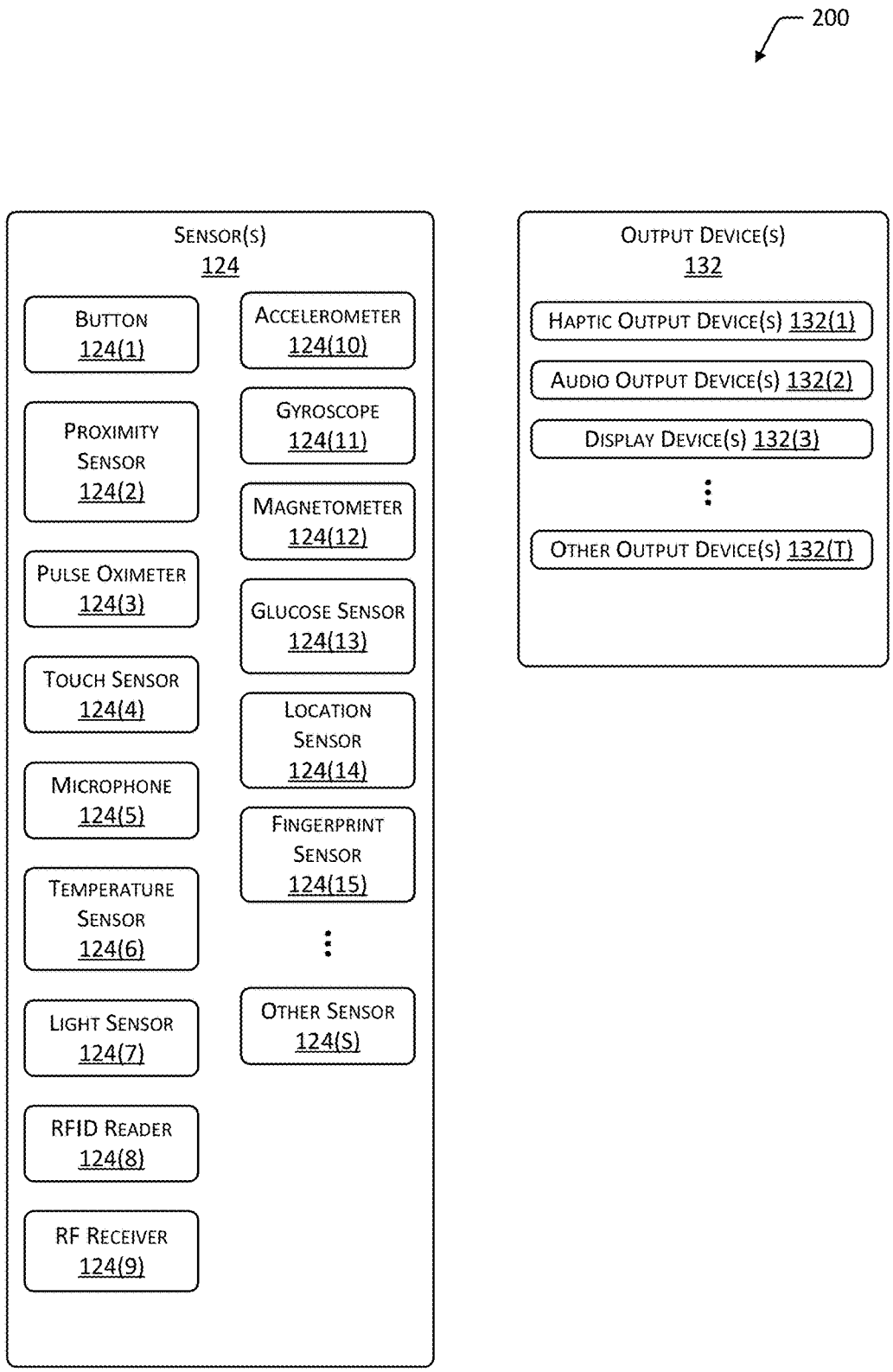
FIG. 2 illustrates a block diagram of sensors and output devices that may be used by computing device(s) during operation.

FIG. 2 illustrates a block diagram 200 of sensors 124 and output devices 132 that may be used by the devices of the system 100 during operation. As described above with FIG. 1, the sensors 124 may generate sensor data 126.

The one or more sensors 124 may be integrated with or internal to the computing device, such as the wearable device 104 or the other device 134. For example, the sensors 124 may be built-in to the computing device during manufacture. In other implementations, the sensors 124 may be part of another device which is configurable to couple to the computing device. For example, the sensors 124 may comprise a device external to, but in communication with, the computing device using Bluetooth, Wi-Fi, 3G, 4G, LTE, ZigBee, Z-Wave, or another wireless or wired communication technology.

The one or more sensors 124 may include one or more buttons 124(1) that are configured to accept input from the user 102. The buttons 124(1) may comprise mechanical, capacitive, optical, or other mechanisms. For example, the buttons 124(1) may comprise mechanical switches configured to accept an applied force from a touch of the user 102 to generate an input signal.

A proximity sensor 124(2) may be configured to provide sensor data 126 indicative of one or more of a presence or absence of an object, a distance to the object, or characteristics of the object. The proximity sensor 124(2) may use optical, electrical, ultrasonic, electromagnetic, or other techniques to determine a presence of an object. For example, the proximity sensor 124(2) may comprise a capacitive proximity sensor configured to provide an electrical field and determine a change in electrical capacitance due to presence or absence of an object within the electrical field.

A pulse oximeter 124(3) may be configured to provide sensor data 126 that is indicative of a cardiac pulse rate and data indicative of oxygen saturation of the user's 102 blood. For example, the pulse oximeter 124(3) may use one or more LEDs and corresponding detectors to determine changes in apparent color of the blood of the user 102 resulting from oxygen binding with hemoglobin in the blood.

The sensors 124 may include one or more touch sensors 124(4). The touch sensors 124(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 124(5) may be configured to acquire information about sound present in the environment. In some implementations, arrays of microphones 124(5) may be used. These arrays may implement beamforming techniques to provide for directionality of gain. The one or more microphones 124(5) may be used to acquire audio data, such as speech from the user 102.

A temperature sensor (or thermometer) 124(6) may provide information indicative of a temperature of an object. The temperature sensor 124(6) in the computing device may be configured to measure ambient air temperature proximate to the user 102, the body temperature of the user 102, and so forth. The temperature sensor 124(6) may comprise a silicon bandgap temperature sensor, thermistor, thermocouple, or other device. In some implementations, the temperature sensor 124(6) may comprise an infrared detector configured to determine temperature using thermal radiation.

The sensors 124 may include one or more light sensors 124(7). The light sensors 124(7) may be configured to provide information associated with ambient lighting conditions such as a level of illumination. The light sensors 124(7) may be sensitive to wavelengths including, but not limited to, infrared, visible, or ultraviolet light. In contrast to the IR camera 108, the light sensor 124(7) may typically provide a sequence of amplitude (magnitude) samples, while the IR camera 108 provides a sequence of two-dimensional frames of samples (pixels).

One or more radio frequency identification (RFID) readers 124(8), near field communication (NFC) systems, and so forth, may also be included as sensors 124. The user 102, objects around the computing device, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise an RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

One or more RF receivers 124(9) may also be included as sensors 124. In some implementations, the RF receivers 124(9) may be part of transceiver assemblies. The RF receivers 124(9) may be configured to acquire RF signals associated with Wi-Fi, Bluetooth, ZigBee, Z-Wave, 3G, 4G, LTE, or other wireless data transmission technologies. The RF receivers 124(9) may provide information associated with data transmitted via radio frequencies, signal strength of RF signals, and so forth. For example, information from the RF receivers 124(9) may be used to facilitate determination of a location of the computing device, and so forth.

The sensors 124 may include one or more accelerometers 124(10). The accelerometers 124(10) may provide information such as the direction and magnitude of an imposed acceleration. Data such as rate of acceleration, determination of changes in direction, speed, and so forth, may be determined using the accelerometers 124(10).

A gyroscope 124(11) provides information indicative of rotation of an object affixed thereto. For example, the gyroscope 124(11) may indicate whether the device has been rotated.

A magnetometer 124(12) may be used to determine an orientation by measuring ambient magnetic fields, such as the terrestrial magnetic field. For example, output from the magnetometer 124(12) may be used to determine whether the device containing the sensor 124, such as the computing device, has changed orientation or otherwise moved. In other implementations, the magnetometer 124(12) may be configured to detect magnetic fields generated by another device.

A glucose sensor 124(13) may be used to determine a concentration of glucose within the blood or tissues of the user 102. For example, the glucose sensor 124(13) may comprise a near infrared spectroscope that determines a concentration of glucose or glucose metabolites in tissues. In another example, the glucose sensor 124(13) may comprise a chemical detector that measures presence of glucose or glucose metabolites at the surface of the user's skin.

A location sensor 124(14) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 124(14) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 124(14) may be omitted or operate in conjunction with an external resource such as a cellular network operator providing location information, or Bluetooth beacons.

A fingerprint sensor 124(15) is configured to acquire fingerprint data. The fingerprint sensor 124(15) may use an optical, ultrasonic, capacitive, resistive, or other detector to obtain an image or other representation of features of a finger. For example, the fingerprint sensor 124(15) may comprise a capacitive sensor configured to generate an image of the fingerprint of the user 102.

The sensors 124 may include other sensors 124(S) as well. For example, the other sensors 124(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 124 may include hardware processors, memory, and other elements configured to perform various functions. Furthermore, the sensors 124 may be configured to communicate by way of a network or may couple directly with the computing device.

The computing device may include or may couple to one or more output devices 132. The output devices 132 are configured to generate signals which may be perceived by the user 102, detectable by the sensors 124, or a combination thereof.

Haptic output devices 132(1) are configured to provide a signal, which results in a tactile sensation to the user 102. The haptic output devices 132(1) may use one or more mechanisms such as electrical stimulation or mechanical displacement to provide the signal. For example, the haptic output devices 132(1) may be configured to generate a modulated electrical signal, which produces an apparent tactile sensation in one or more fingers of the user 102. In another example, the haptic output devices 132(1) may comprise piezoelectric or rotary motor devices configured to provide a vibration that may be felt by the user 102.

One or more audio output devices 132(2) are configured to provide acoustic output. The acoustic output includes one or more of infrasonic sound, audible sound, or ultrasonic sound. The audio output devices 132(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 132(2).

The display devices 132(3) may be configured to provide output that may be seen by the user 102 or detected by a light-sensitive detector such as the image sensor 110 or light sensor 124(7). The output may be monochrome or color. The display devices 132(3) may be emissive, reflective, or both. An emissive display device 132(3), such as using light emitting diodes (LEDs), is configured to emit light during operation. In comparison, a reflective display device 132(3), such as using an electrophoretic element, relies on ambient light to present an image. Backlights or front lights may be used to illuminate non-emissive display devices 132(3) to provide visibility of the output in conditions where the ambient light levels are low.

The display mechanisms of display devices 132(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 132(3) may operate as panels, projectors, and so forth.

The display devices 132(3) may be configured to present images. For example, the display devices 132(3) may comprise a pixel-addressable display. The image may comprise at least a two-dimensional array of pixels or a vector representation of an at least two-dimensional image.

In some implementations, the display devices 132(3) may be configured to provide non-image data, such as text or numeric characters, colors, and so forth. For example, a segmented electrophoretic display device 132(3), segmented LED, and so forth, may be used to present information such as letters or numbers. The display devices 132(3) may also be configurable to vary the color of the segment, such as using multicolor LED segments.

Other output devices 132(T) may also be present. For example, the other output devices 132(T) may include scent/odor dispensers.

Figure 3:
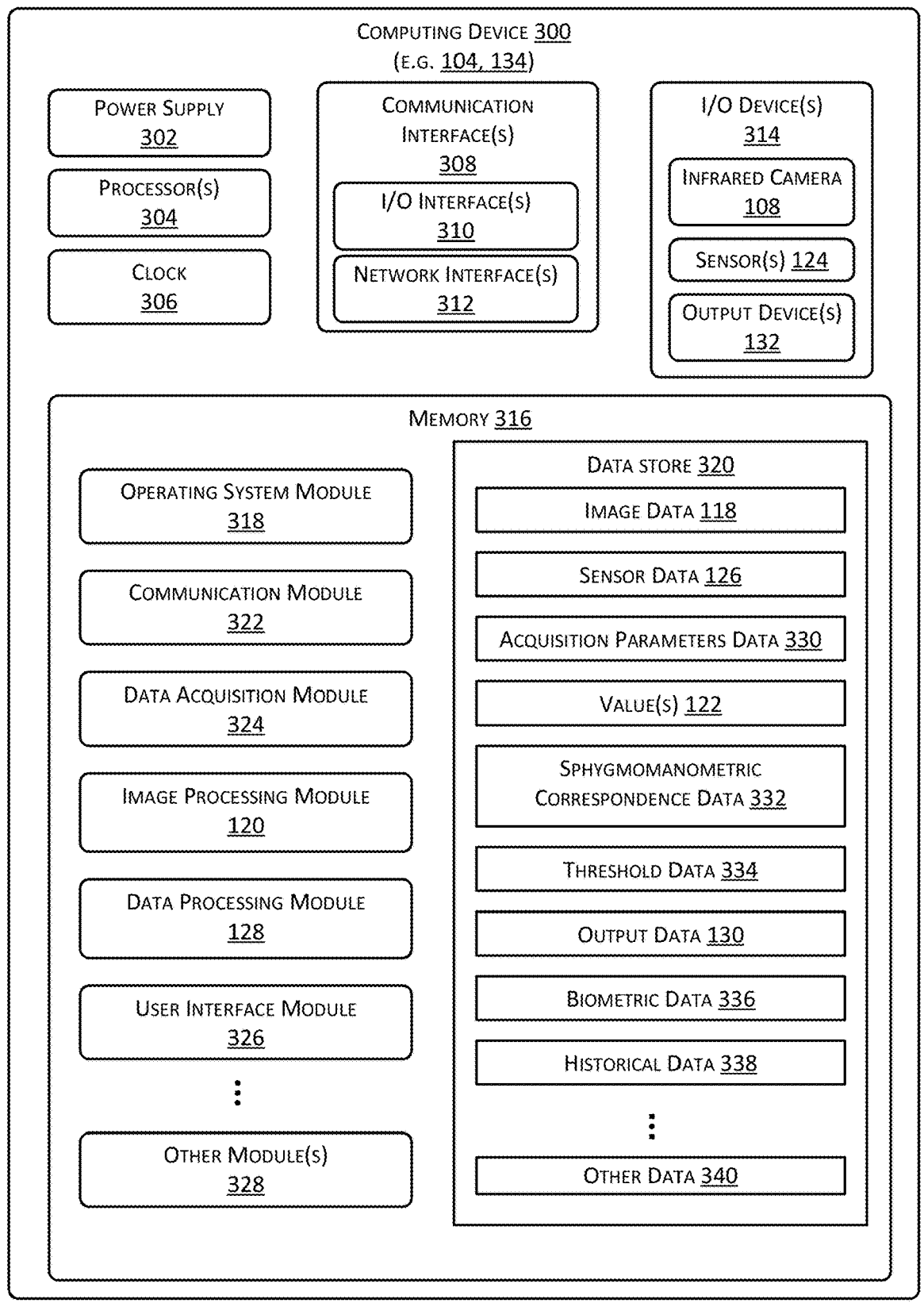
FIG. 3 illustrates a block diagram of a computing device(s) that may be included in or in communication with the wearable device, according to one implementation.

FIG. 3 illustrates a block diagram of a computing device 300 configured to support operation of the system 100. As described above, the computing device 300 may be the wearable device 104, the other device 134, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of the IR camera 108, a sensor 124, keyboard, mouse, scanner, and so forth. The I/O devices 314 may also include output devices 132 such as one or more of a display device 132(3), printer, audio output device 132(2), and so forth. In some embodiments, the I/O devices 314 may be physically incorporated with the computing device 300 or may be externally placed.

The network interfaces 312 are configured to provide communications between the computing device 300 and other devices, such as the sensors 124, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more buses or other internal communications hardware or software that allow for the transfer of data between the various modules and components of the computing device 300.

As shown in FIG. 3, the computing device 300 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Wash., USA; the Android operating system from Google Corporation of Mountain View, Calif., USA; the iOS operating system from Apple Corporation of Cupertino, Calif., USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including other computing devices 300, network attached storage devices, and so forth.

A communication module 322 may be configured to establish communications with one or more of other computing devices 300, the sensors 124, or other devices 134. The communications may be authenticated, encrypted, and so forth. The communication module 322 may also control the communication interfaces 308.

Acquisition parameter data 330 may be stored in the memory 316. The acquisition parameter data 330 may comprise parameters such resolution, frame rate, duration, or other settings that are used to operate the infrared camera 108. For example, the acquisition parameter data 330 may indicate that the IR camera 108 is to generate image data 118 that is at the highest available resolution from the image sensor 124, at 30 frames per second (fps) for 10 seconds.

The memory 316 may also store a data acquisition module 324. The data acquisition module 324 is configured to acquire image data 118 from the infrared camera 108, sensor data 126 from the one or more sensors 124, and so forth. In some implementations, the data acquisition module 324 may perform some processing of the sensor data 126. For example, an image rectification function may be applied to map raw image data 118 from the IR camera 108 to a rectilinear format, compensating for the "fisheye effect" produced by the wide-angle lens(es) 112 of the IR camera 108.

In some implementations, the data acquisition module 324 may be configured to operate the IR camera 108 to acquire image data 118. For example, if the data acquisition module 324 determines that the sensor data 126 is indicative of a trigger event, the IR camera 108 may be operated to acquire image data 118. The trigger event may comprise values of sensor data 126 for one or more sensors 124 exceeding a threshold value. For example, if the temperature sensor 124(6) indicates that the temperature of the user 102 has exceeded a threshold value, the IR camera 108 may be operated to generate image data 118.

The image data 118 comprises one or more images that are obtained at different times. For example, the image data 118 may comprise images obtained at successive times. The image processing module 120 is configured to determine one or more features present in one or more images. These features may include blood vessels, or portions thereof.

The image processing module 120 generates one or more values 122 based on the image data 118. For example, the image processing module 120 may use edge detection algorithms to determine the edges of blood vessels in the image data 118. Once the edges of a blood vessel have been determined, a distance between the edges of the blood vessel may be determined. The distance may be determined with respect to pixels, a linear measurement such as millimeters, or other metric.

The memory 316 may also store the data processing module 128. The data processing module 128 may use the values 122 as input. In one implementation, the data processing module 128 may use sphygmomanometric correspondence data 332 to generate output data 130 that is indicative of a blood pressure of the user 102, based on the image data 118. For example, a calibration process may be performed in which an external sphygmomanometer is used to obtain sphygmomanometric data indicative of blood pressure data such as systolic and diastolic pressure at a given time. At a contemporaneous time, the infrared camera 108 may be used to obtain the image data 118. The sphygmomanometric data may be used in conjunction with the values 122 obtained from the image data 118 to determine a correspondence between one or more values 122 and the blood pressure. This correspondence may be stored as the sphygmomanometric correspondence data 332. The sphygmomanometric correspondence data 332 may be specific to a particular user 102, to position of the IR camera 108 with respect to the user 102, and so forth. For example, the sphygmomanometric correspondence data 332 may be specific to a left wrist of user "Alex". In some implementations, the sphygmomanometric correspondence data 332 may be processed using one or more techniques to interpolate values between those which have been measured.

Threshold data 334 may be stored in the memory 316. The threshold data 334 may be used to designate threshold values to which image data 118, sensor data 126, values 122, and so forth may be compared. For example, the threshold data 334 may specify one or more threshold values for one or more values 122, that when exceeded, trigger presentation of output to the user 102.

The output data 130 may be presented using one or more of the output devices 132, transmitted to the other devices 134, and so forth. As described above, if the one or more values 122 exceed a threshold value, an output device 132 may present an alarm to the user 102. For example, the values 122 may be indicative of a first distance across a blood vessel at a first time and a second distance at the blood vessel at a second. A change value may be determined by calculating a difference between the first distance and the second distance. If the change value exceeds a threshold value, an alarm may be presented to the user 102.

A user interface module 326 provides a user interface using one or more of the I/O devices 314. The user interface module 326 may be used to obtain input from the user 102, present information to the user 102, and so forth. For example, the user interface module 326 may present a graphical user interface on the display device 132(3) and accept user input using the touch sensor 124(4).

Continuing the earlier example, if the user's 102 blood pressure is determined to exceed a threshold value, the user interface module 326 may present information indicative of this on the display device 132(3). The user 102 may then cease activity, engage in a calming activity, and so forth, to reduce their blood pressure.

In some implementations the wearable device 104 may be used to generate biometric data 336. For example, information such as the particular arrangement of blood vessels, changes in the values 122 over time, and so forth, may be used as biometric indicia. The biometric indicia may be indicative of a particular user, or a portion thereof such as differentiating a left arm from a right arm. The biometric indicia may be used to identify the user 102, or a portion thereof. For example, the biometric indicia may be used to retrieve the sphygmomanometric correspondence data 332 that is associated with that particular user 102 and the particular arm that they are wearing the wearable device 104 on at that time.

The computing device 300 may maintain historical data 338. For example, the historical data 338 may comprise the values 122 or data based at least in part on the values that have been obtained at different dates and times. The historical data 338 may be used to provide information about trends or changes over time. For example, the historical data 338 may comprise an indication of an average blood pressure of the user 102 over a span of several months. The user 102 may then use this data to assist in managing their activities.

Other modules 328 may also be present in the memory 316, as well as other data 340 in the data store 320.

In different implementations, different computing devices 300 may have different capabilities or capacities. For example, the other device 134 may have significantly more processor 304 capability and memory 316 capacity compared to the wearable device 104. In one implementation, the wearable device 104 may determine the values 122 and send those values 122 to the other device 134. In another implementation, the wearable device 104 may obtain the image data 118 which is then sent to the other device 134 for processing to determine the values 122. Other combinations of distribution of data processing and functionality may be used in other implementations.

Figure 4:
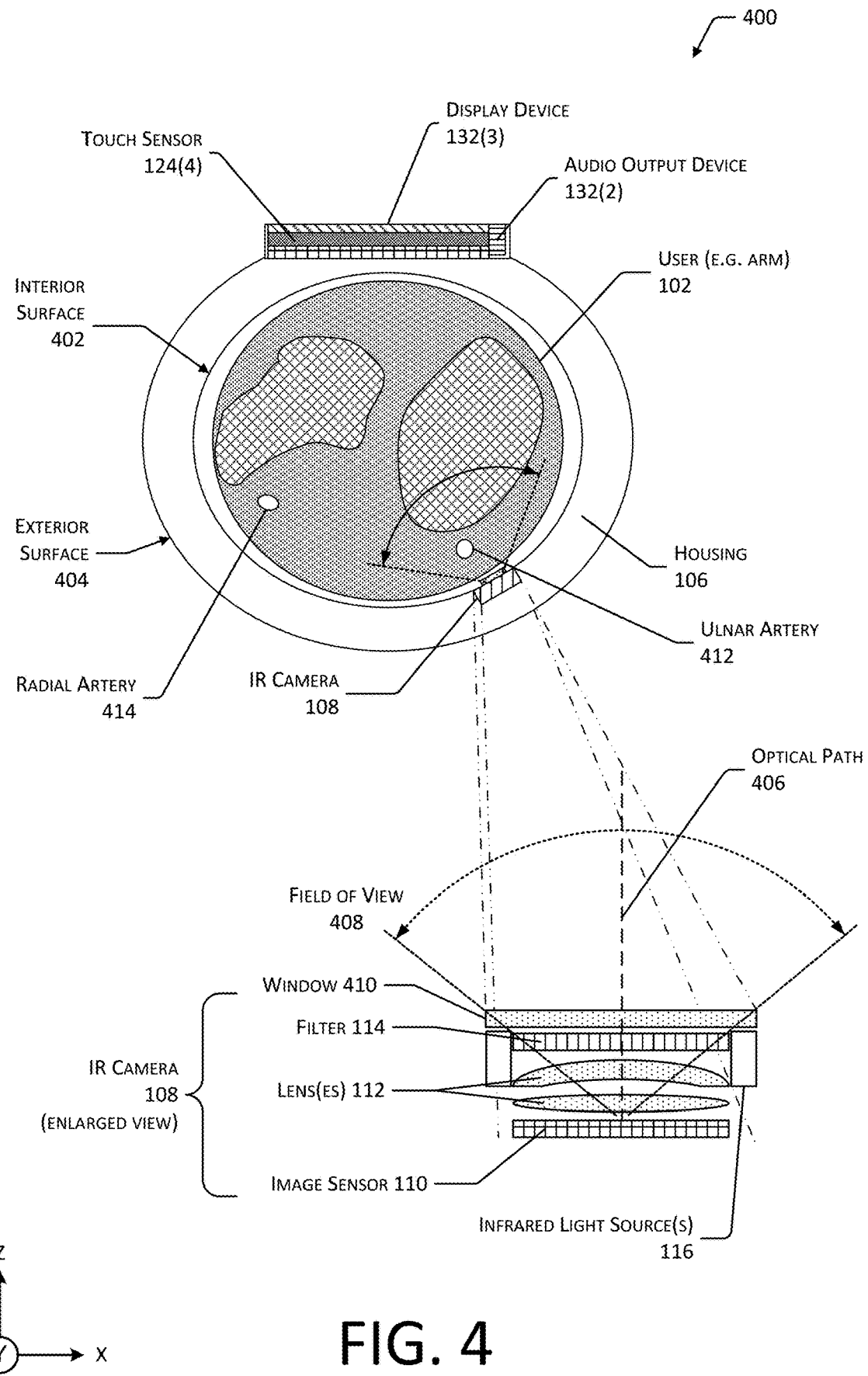
FIG. 4 illustrates a wearable device with an infrared camera to obtain images of blood vessels in a user's limb, according to one implementation.

FIG. 4 illustrates one implementation 400 of the wearable device 104 with an infrared camera 108 to obtain images of blood vessels in a user's limb. This illustration depicts a side or cross-sectional view of a wearable device 104 configured to be worn around an arm or leg of the user 102. In other implementations other configurations may be used. For example, the wearable device 104 may comprise a neckband that is worn on the neck or a headband that is worn on the head.

The wearable device 104 may comprise structures made of one or more of metal, plastic, ceramic, composite, or other material. These structures may include one or more members configured to maintain the wearable device 104 or a portion thereof proximate to the user 102. For example, one or more members may include arms, straps, pins, snaps, adhesives, mechanical interface fixtures, clamps, and so forth. The members may be engaged when they couple to at least a portion of the user 102, clothing of the user 102, and so forth. For example, the members may comprise straps to be worn and latched around the wrist of the user 102. One or more latches may be configured to selectively join or disjoin members from one another or from other structures, allowing the wearable device 104 to be donned or doffed.

In the implementation depicted here, the wearable device 104 comprises a housing 106. The housing 106 may comprise one or more elements configured to encircle at least a portion of the forearm or wrist of the user 102 and maintain the wearable device 104 proximate to the user 102. The housing 106 may comprise a series of links of rigid material or may comprise one or more pieces of elastomeric material. For example, the housing 106 may include a series of metal links or may comprise a single piece of silicone rubber.

The housing 106 includes an interior surface 402 and an exterior surface 404. During normal use, the interior surface 402 is proximate to the skin of the user 102.

The wearable device 104 may include one or more sensors 124. For example, the wearable device 104 depicted includes a touch sensor 124(4). The wearable device 104 may also comprise output devices 132. For example, the wearable device 104 depicted here includes a display device 132(3) such as an LED display and an audio output device 132(2) such as a speaker. Other output devices 132 such as haptic output devices 132(1) may also be present but are not depicted in this illustration.

The wearable device 104 includes the IR camera 108. The IR camera 108 may be arranged in different positions with respect to the user's arm 102. In this illustration, the IR camera 108 is positioned during wear proximate to an inner surface of the wrist and one or more of the radial artery 414 or the ulnar artery 412. In other implementations, the IR camera 108 may be positioned elsewhere during wear, such as on an outer surface of the wrist, opposite the inner surface.

As shown in an enlarged view, the IR camera 108 includes an image sensor 110, one or more lenses 112, and may include one or more filters 114. An optical path 406 extends from the image sensor 110, and a field of view 408 of the IR camera 108 is shown. In one implementation, the field of view 408 of the IR camera 108 may be greater than or equal to 90 degrees in one plane that extends perpendicular to a plane of the image sensor 110.

The image sensor 110 may comprise a CMOS sensor with a resolution of 400×400 pixels and a global shutter. For example, the image sensor 110 may comprise part number OV6211 from OmniVision Technologies, Inc. In other implementations, other types of image sensors 110 may be used. For example, the image sensor 110 may comprise a CMOS device with a rolling shutter.

The one or more lenses 112 may be configured to produce a wide-angle FOV 408. The use of a wide-angle FOV 408 increases the area of the user 102 that is depicted in the image data 118. The use of lenses 112 that produce a wide-angle FOV 408 may also provide sufficient depth of field in which features such as the blood vessels are in focus.

The filter 114 may comprise a bandpass filter that is configures to transmit light with wavelengths between a first wavelength and a second wavelength, such as 700 nm to 1000 nm, while attenuating other wavelengths. The filter 114 may be configured such that the bandpass corresponds to the wavelength produced by the IR light source(s) 116.

A window 410 may be present in the optical path 406. The window 410 prevents contaminants in the external environment from entering the IR camera 108, housing 106, or both. In some implementations the window 410 may comprise or act as the filter 114, a lens 112, or both. The window 410 may be configured to extend or protrude at least slightly with respect to the interior surface 402. During use the window 410 may be in contact with the skin of the user 102. The window 410 may include one or more coatings, such as a coating to improve scratch resistance.

The IR camera 108 may include, or operate in conjunction with, one or more IR light sources 116. The IR light sources 116 are configured to produce near IR light that is detectable by the image sensor 110. The IR light sources 116 may comprise light emitting diodes (LED), quantum dots, and so forth.

In the implementation depicted here, the IR light sources 116 are positioned inside the housing 106, behind the window 410. The light they emit passes through the window 410, illuminates at least a portion of the user 102, and at least a portion of the reflected light returns through the window 410, passes through the filter 114 and lenses 112 and is then detected by the image sensor 110. In other implementations, the IR light sources 116 may be positioned elsewhere. For example, the IR light sources 116 may be located elsewhere within the housing 106 and use separate lenses, windows, optical waveguides, and so forth to deliver light that illuminates a portion of the user 102. In one implementation, the IR light sources 116 may be used to transilluminate at least a portion of the user 102.

Other electronics may also be present in the wearable device 104. For example, the other electronics may include one or more of the elements associated with a computing device 300 described with regard to FIG. 3.

Figure 5:
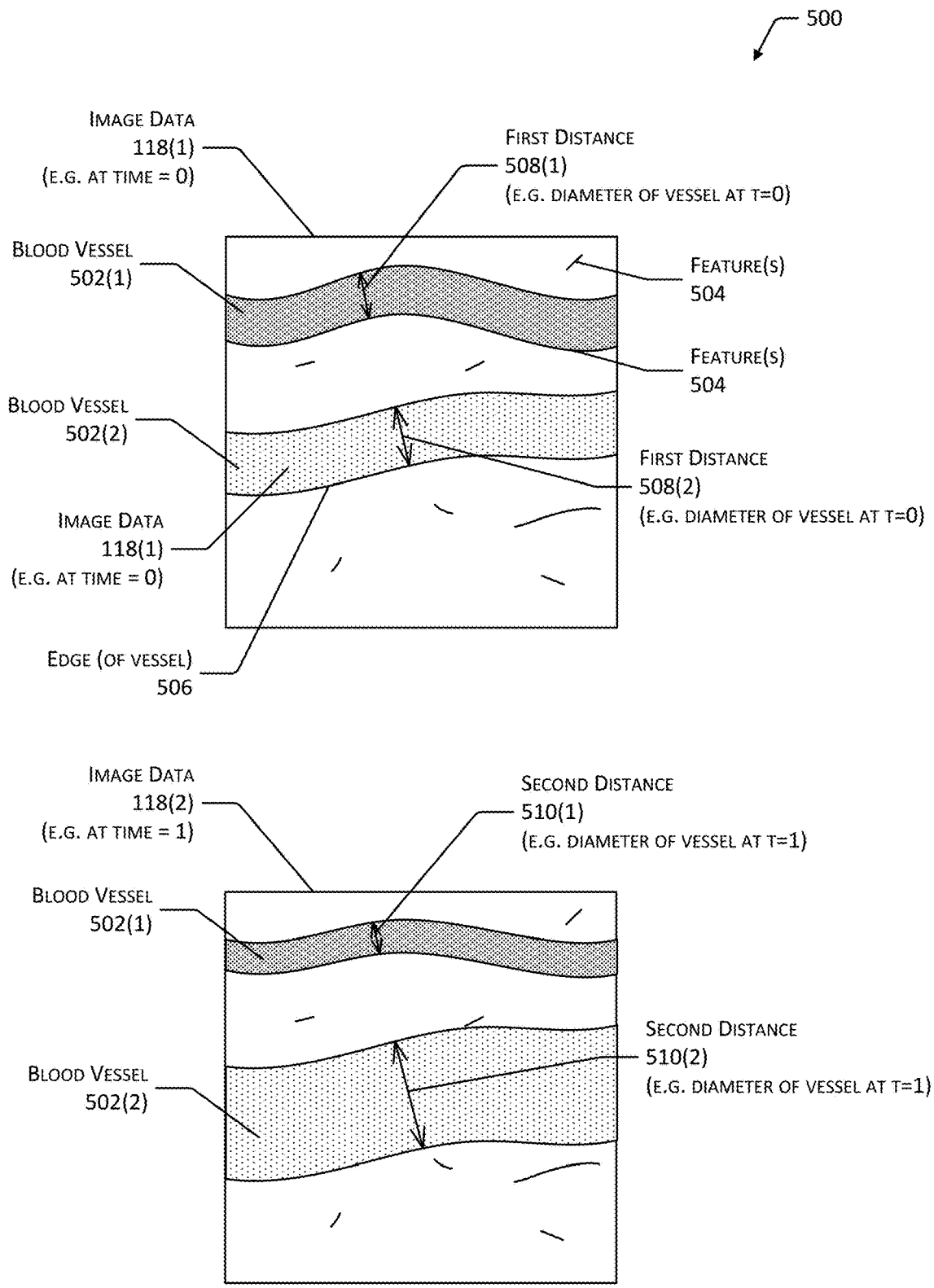
FIG. 5 illustrates example images obtained by the infrared camera, according to one implementation.

FIG. 5 illustrates example images 500 obtained by the IR camera 108 at different times, according to one implementation. Image data 118(1) is shown that was obtained at time=0 while image data 118(2) is shown that was obtained at time=1. While two images are depicted, it is understood that any number of images may be processed as determined herein. The image data 118(1) and 118(2) depicted here may be representative of pre-processing. For example, the raw image data 118 obtained from the IR camera 108 may be blurred due to various effects, such as backscatter. The raw image data 118 may be processed using techniques to remove blur, resolve edges, and so forth.

The image data 118 depicts one or more blood vessels 502. For example, image data 118(1) shows a first blood vessel 502(1) and a second blood vessel 502(2). In this illustration, the first blood vessel 502(1) may be a vein (as depicted with darker shading) and the second blood vessel 502(2) may be an artery (as depicted with light shading).

The image processing module 120 may be used to determine one or more features 504. These features 504 may comprise portions of the blood vessels 502, bones, noise, blemishes, and so forth. In one implementation, the image processing module 120 may use an edge detection algorithm, such as a Canny detector, to determine the edges 506 of the blood vessels 502.

Once determined, the image processing module 120 may determine a distance between those features 504. For example, the image processing module 120 may determine a distance 508 from a first edge 506 to a second edge 506 of the blood vessel 502. In this illustration, a first distance 508(1) is shown for the first blood vessel 502(1) and a second distance 508(2) is shown for the second blood vessel 502(2) at time=0. In some implementations the distance 508 may be considered a diameter of the blood vessel 502. However, the actual physical diameter of the blood vessel 502 may vary based on location within the FOV 408, distance from the IR camera 108 to the blood vessel 502, or other factors.

The distance 508 may be determined with respect to pixels, a linear measurement such as millimeters, or other metric. The distance 508 may be considered a shortest distance between two edges 506. Two blood vessels 502(1) and 502(2) and distances 508(1) and 508(2) are depicted for ease of illustration, and not necessarily as a limitation.

The image data 118(2) shows the first blood vessel 502(1) and the second blood vessel 502(2) at time=1. Also shown is a second distance 510(1) of the first blood vessel 502(1) and a second distance 510(2) of the second blood vessel 502(2).

In this illustration, time=0 corresponds to a point in time between successive heartbeats. As a result, the pressure in the vessels is at a minimum at time=0. In comparison, time=1 corresponds to a point in time at which a pressure pulse resulting from a contraction of the heart is at a maximum for the portions of the blood vessels 502 that are depicted.

As a result of the pressure provided by the contraction of the heart, the second distance 510(2) is greater than the first distance 508(2), as the walls of the artery shown as blood vessel 502(2) expands under the force of the pressure. Because the pressure in the venous vessels lags the pressure produced by the contraction, the vein shown as blood vessel 502(1) does not experience a substantial change between the first distance 508(1) and the second distance 510(1).

The image processing module 120 may generate values 122 such as a feature vector that is indicative of a particular feature 504, location of the feature 504 within the image, size of the feature 504 within the image, distance, time, and so forth. For example, the values 122 may indicate that at time=0 the first distance 508(2) of the feature 504 shown as blood vessel 502(2) was 15 pixels, while at time=1 the second distance 510(2) was 28 pixels.

In some implementations other data present in the image data 118 may be used. For example, based on the luminance, chrominance, or other values provided by the image sensor 110, the color value of the blood vessels 502 may be determined. The color value may then be used to determine information such as oxygen saturation of the blood in the blood vessels 502. Continuing the example, veins may be distinguished from arteries based at least in part on their apparent color.

In some implementations, blood vessels 502 may be categorized as arteries or veins based on the relative change in distances over time. For example, an artery may experience a greater percentage change in distance from minimum to maximum than a vein. Such a determination may include determining a first distance indicative of a distance from a first edge to a second edge of the first blood vessel at a first time. A second distance indicative of a distance from a third edge to a fourth edge of the second blood vessel at the first time is determined. A third distance is determined that is indicative of a distance from the first edge to the second edge of the first blood vessel at the second time. A fourth distance indicative of a distance from the third edge to the fourth edge of the second blood vessel at the second time is determined. The first distance is determined to be greater than the second distance, and the third distance is greater than the fourth distance. The first blood vessel may then be categorized as an artery. Measurements may be taken of different categories of blood vessel 502 and analyzed. For example, measurements of both the artery and the vein may be obtained at different times, and a delay and attenuation between the two correlated to one or more metabolic conditions.

Figure 6:
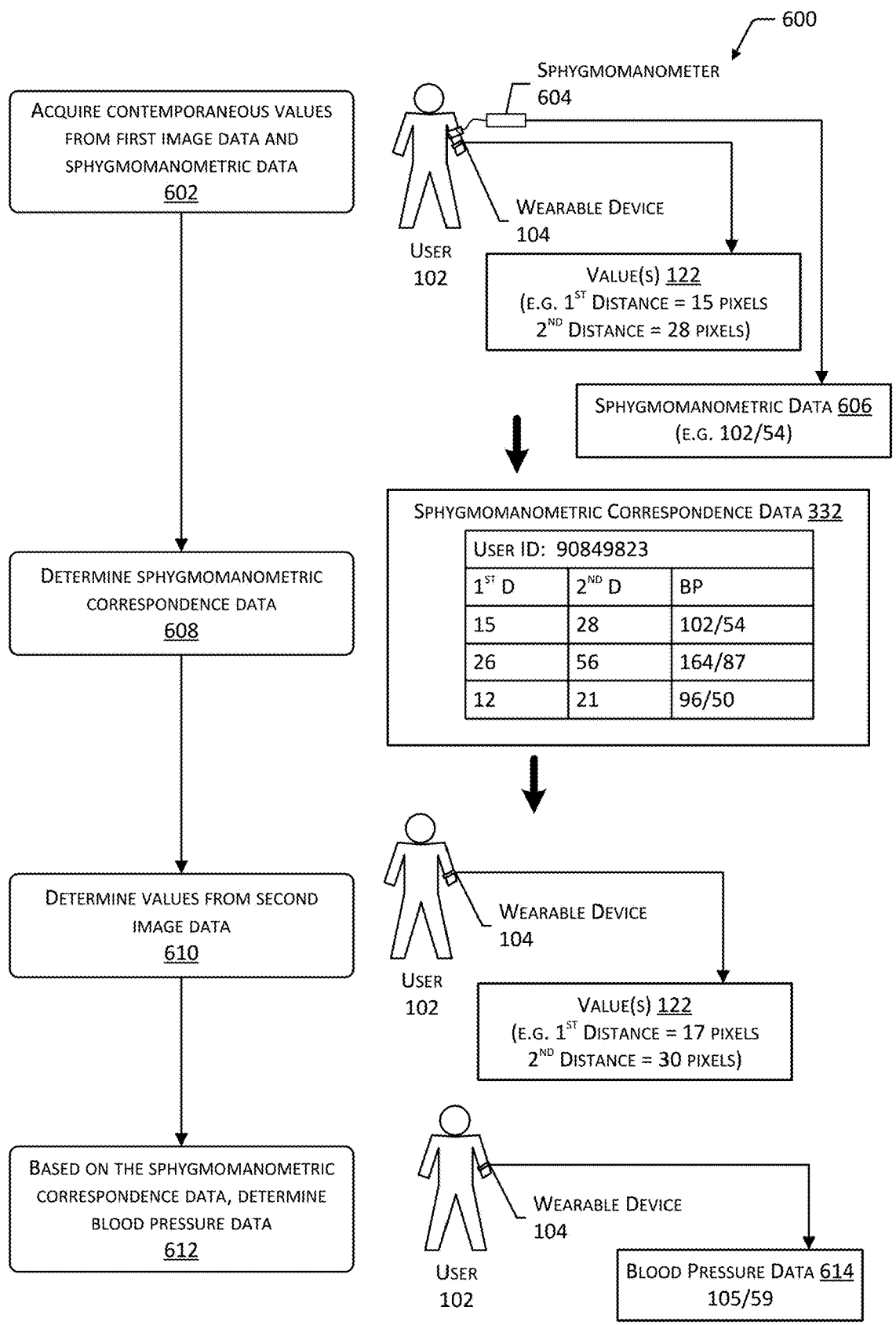
FIG. 6 illustrates a scenario in which values gathered by the wearable device and from a separate sphygmomanometer are acquired and used to generate correspondence data that is subsequently used to infer blood pressure data from infrared images, according to one implementation.

FIG. 6 illustrates a scenario 600 in which values gathered by the wearable device 104 and from a separate sphygmomanometer are acquired and used to generate sphygmomanometric correspondence data 332 that is subsequently used to infer blood pressure data from infrared images, according to one implementation.

At 602, during a calibration process, contemporaneous values 122 are obtained from first image data 118 as described above while a sphygmomanometer 604 is used to acquire sphygmomanometric data 606. For example, the sphygmomanometric data 606 may indicate a blood pressure of 102 systolic and 54 diastolic. In the illustration depicted here, the first image data 118 is obtained at a first time and the sphygmomanometric data 606 is obtained at another time before or after the first time. In another example, the wearable device 104 may be located on a right arm while the sphygmomanometer is on a left arm and the first image data 118 and the sphygmomanometric data 606 may be obtained simultaneously. In one implementation, the wearable device 104 and the sphygmomanometer 604 may be in communication with one another. For example, the wearable device 104 may use Bluetooth to communicate with the sphygmomanometer 604. The wearable device 104 may send an instruction to the sphygmomanometer 604 to initiate operation and generate sphygmomanometric data 606. The sphygmomanometer 604 may then send the sphygmomanometric data 606 to the wearable device 104 using Bluetooth.

In some implementations, image data 118 may be obtained while the sphygmomanometer 604 cuff is at maximum pressure, at which time the artery is considered fully occluded. The resulting image data 118 may be processed to determine values 122 associated with a lowest or minimum pressure applied to the artery.

At 608 sphygmomanometric correspondence data 332 is determined. In one implementation, values 122 and sphygmomanometric data 606 may be obtained at various different times and under different conditions. For example, the user interface module 326 may use the display device 132(3) on the wearable device 104 to provide directions such as "stand up", "sit down", "walk around", "lay down" to the user 102. The user 102 may then comply, and another set of measurements may be obtained by the wearable device 104 and the sphygmomanometer 604. Once several sets of data have been determined, one or more techniques may be used to determine a correspondence between one or more of the values 122 and blood pressure as indicated by the sphygmomanometric data 606. Data representative of this correspondence may then be stored as the sphygmomanometric correspondence data 332.

At 610, at a time after the calibration process, second image data 118 is obtained and second values 122 are determined.

At 612, the second values 122 are used in conjunction with the sphygmomanometric correspondence data 332 to determine blood pressure data 614. For example, the second values 122 may be used as inputs to an interpolation function that associates the values with blood pressure.

In some implementations the calibration process may be performed at other times. For example, to maintain accuracy of the blood pressure data 614 over time, the process of acquiring the sphygmomanometric data 606 and determining the sphygmomanometric correspondence data 332 may be performed daily or weekly.

Figure 7:
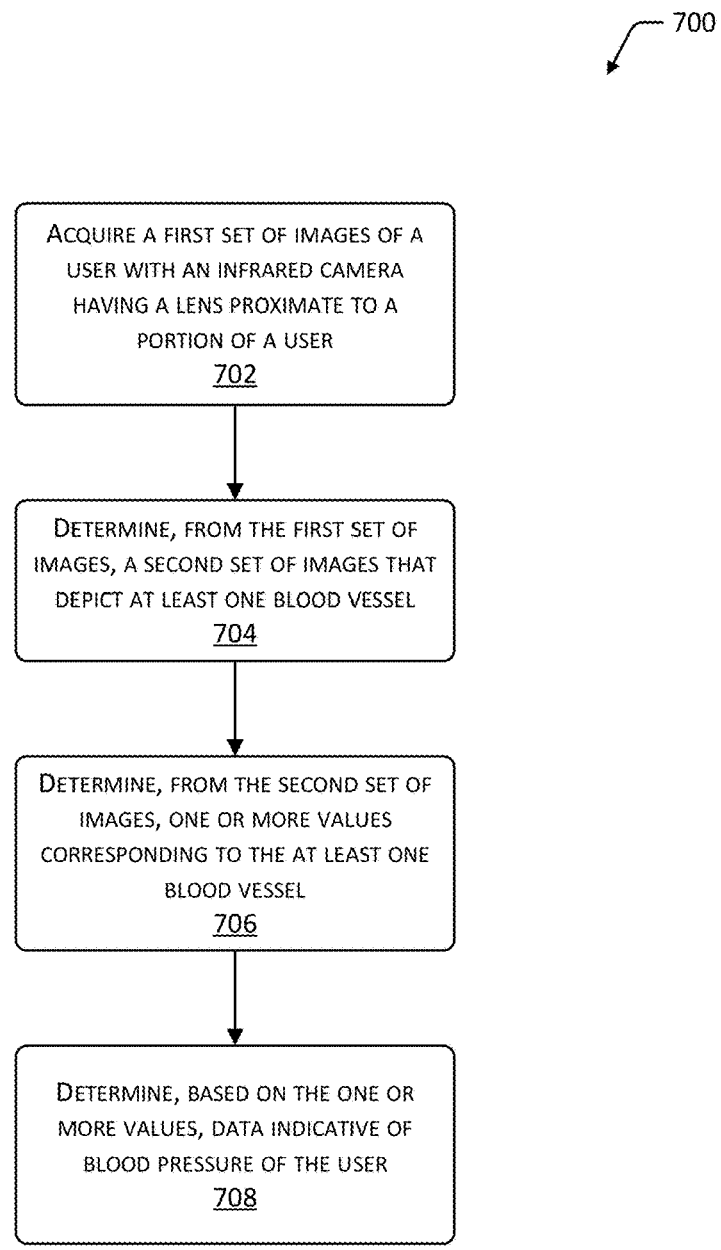
FIG. 7 illustrates a flow diagram of a process of a wearable device using image data obtained from an infrared camera to determine blood pressure data, according to one implementation.

FIG. 7 illustrates a flow diagram 700 of a process of a wearable device 104 using image data 118 obtained from an infrared camera 108 to determine blood pressure data 614, according to one implementation. The process may be performed by one or more of the wearable device 104 or other devices 134.

At 702 image data 118 comprising a first set of images is acquired with an IR camera 108. As described above, the IR camera 108 may have a lens 112 that is proximate to the user 102, such that a FOV 408 of the IR camera 108 includes at least a portion of the user 102. Each image in the image data 118 may be obtained at different times.

In some implementations, the acquisition of the image data 118 may be triggered responsive to data from one or more of the sensors 124. For example, the pulse oximeter 124(3) may determine data indicative of a time series of pulse events corresponding to contractions of the user's 102 heart. The time series may be used to determine a pattern that is then used to predict when the next contraction will take place. The IR camera 108 may then be operated to acquire image data 118 at a particular time, based on the prediction. For example, the IR camera 108 may be triggered by the prediction of the contractions to acquire image data 118 comprising a single image at a time that is predicted. By using this technique, the wearable device 104 may reduce the amount of data being processed, minimize power consumption, and so forth. For example, where the image data 118 comprises a video clip the images may be processed to determine those images in which the artery exhibited a maximum distance. In comparison, by using another sensor 124 or a prediction based on data from the sensor(s) 124, the wearable device 104 may reduce the amount of data processed.

At 704, a second set of images are determined from the first set of images that depict at least one blood vessel 502. For example, the second set if images may discard those images that have contrast below a threshold value, are deemed too blurry, do not include features 504 that exceed a threshold minimum area within the image, have feature descriptors that do not match previously set values, and so forth.

At 706, from the second set of images, one or more values 122 corresponding to the at least one blood vessel 502 are determined. For example, the distance 508 from one edge 506 of a blood vessel 502 to another may be determined. In some implementations, the distance may be determined as a shortest distance between two linear features, wherein each linear feature exhibits a length that exceeds a threshold value.

In one implementation, the one or more values 122 may be determined for each image. These values 122 may then be processed to determine minima, maxima, and so forth. For example, if the one or more values 122 from the second set of images is indicative of the distance from one edge 506 of a vessel to another, the maximum distance and the minimum distance may be determined. The maximum distance may be used to determine a systolic blood pressure value while a minimum distance may be used to determine a diastolic blood pressure value. The minima and maxima may be determined for an entire set of values, or may comprise a local minima and local maxima over shorter windows of time.

At 708, based at least in part on the one or more values 122, data indicative of the physical condition of the user 102 is determined. For example, the values 122 may be used as input to the sphygmomanometer correspondence data 332 and blood pressure data 614 produced as an output. In some implementations other data, such as a confidence value may be produced. For example, the blood pressure data 614 may indicate a systolic pressure estimate, a diastolic pressure estimate, and data indicative of accuracy of the estimates.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
   a band having an exterior surface and an interior surface that is proximate to a wrist of a user;
   a camera coupled to the interior surface of the band at a location that is proximate to one or more of a radial artery or an ulnar artery, the camera comprising:
   an image sensor to detect infrared light;
   a lens having a field of view with an angle that is greater than 90 degrees as measured diagonally across opposite corners of the field of view, wherein the lens is arranged proximate to the interior surface, such that the field of view includes a portion of the wrist; and
   an infrared light source to illuminate at least a portion of the field of view with infrared light;
   a first clock;
   a first memory storing computer-executable instructions; and
   a first hardware processor, wherein the first hardware processor is configured to execute the computer-executable instructions to:
   acquire a first image obtained by the camera at a first time at a first pressure;
   determine a first edge and a second edge of a first blood vessel depicted in the first image;
   determine a first distance between the first edge and the second edge of the first blood vessel depicted in the first image, wherein the first distance is a shortest distance between the first edge and the second edge;
   determine a third edge and a fourth edge of a second blood vessel depicted in the first image;
   determine a second distance between the third edge and the fourth edge of the second blood vessel depicted in the first image, wherein the second distance is a shortest distance between the third edge and the fourth edge;
   acquire a second image obtained by the camera at a second time at a second pressure, wherein the second pressure is greater than the first pressure;
   determine the first edge and the second edge of the first blood vessel depicted in the second image;
   determine a third distance between the first edge and the second edge of the first blood vessel depicted in the second image, wherein the third distance is a shortest distance between the first edge and the second edge;
   determine the third edge and the fourth edge of the second blood vessel depicted in the second image;
   determine a fourth distance between the third edge and the fourth edge of the second blood vessel depicted in the second image, wherein the fourth distance is a shortest distance between the third edge and the fourth edge;
   determine a first relative change in distance of the first blood vessel from the first time to the second time based on the first distance and the third distance;
   determine a second relative change in distance of the second blood vessel from the first time to the second time based on the second distance and the fourth distance;
   determine the first relative change in distance of the first blood vessel is greater than the second relative change in distance of the second blood vessel;
   determine the first blood vessel is an artery based on the first relative change in distance of the first blood vessel being greater than the second relative change in distance of the second blood vessel;
   retrieve, using the first distance, a systolic pressure value from stored data, the systolic pressure value corresponding to the first time; and
   retrieve, using the second distance, a diastolic pressure value from the stored data, the diastolic pressure value corresponding to the first time.

2. The wearable device of claim 1, further comprising a communication interface; and the first hardware processor to further execute the computer-executable instructions to:
   receive, via the communication interface, blood pressure data from a sphygmomanometer, the blood pressure data derived from a plurality of images obtained at one or more different times, wherein the blood pressure data is indicative of a corresponding systolic blood pressure value and a corresponding diastolic blood pressure value at the one or more different times;
   determine edges of a particular blood vessel depicted in the plurality of images;
   determine a set of distances indicative of a shortest distance between the edges depicted in the plurality of images;
   determine a correspondence between the set of distances and the blood pressure data; and
   store the correspondence as the stored data.

3. A system comprising:
   a first device comprising:
   a band having an exterior surface and an interior surface proximate to a wrist of a user;
   a camera coupled to the interior surface of the band and facing a lower portion of the wrist of the user, the camera comprising:
   an image sensor to detect infrared light;
   a lens arranged proximate to the interior surface, such that a field of view of the camera includes a portion of the user; and
   a light source to illuminate at least a portion of the field of view with infrared light;

a communication interface; and
a computing device comprising:
  a memory storing computer-executable instructions; and
  a hardware processor, wherein the hardware processor is configured to execute the computer-executable instructions to:
    acquire a first set of images from the camera, wherein each image in the first set of images is obtained at a different time;
    determine, from the first set of images, a second set of images, wherein the second set of images includes:
      a first image acquired at a first time that depicts a first blood vessel and a second blood vessel at a first pressure, and
      a second image acquired at a second time that depicts the first blood vessel and the second blood vessel at a second pressure, wherein the second pressure is greater than the first pressure;
    determine a first distance associated with the first blood vessel at the first time;
    determine a second distance associated with the second blood vessel at the first time;
    determine a third distance associated with the first blood vessel at the second time;
    determine a fourth distance associated with the second blood vessel at the second time;
    determine a first relative change in distance of the first blood vessel from the first time to the second time based on the first distance and the third distance;
    determine a second relative change in distance of the second blood vessel from the first time to the second time based on the second distance and the fourth distance;
    determine the first relative change in distance of the first blood vessel is greater than the second relative change in distance of the second blood vessel; and
    determine the first blood vessel is an artery based on the first relative change in distance of the first blood vessel being greater than the second relative change in distance of the second blood vessel.

4. The system of claim 3, wherein the first distance represents a distance extending from a first wall of the first blood vessel to a second wall of the first blood vessel that is opposite the first wall.

5. The system of claim 3, the hardware processor to further execute the computer-executable instructions to:
  determine a percentage change in diameter from a minimum diameter to a maximum diameter of the first blood vessel.

6. The system of claim 3, the hardware processor to further execute the computer-executable instructions to:
  determine a ratio of a first diameter associated with the first blood vessel to a second diameter associated with the second blood vessel depicted in the first image.

7. The system of claim 3, the first device further comprising:
  a window that is arranged in an optical path between the lens and the interior surface, wherein the window is transparent to the infrared light and a portion of the window that is proximate to the interior surface is flat;
  a filter that is arranged in the optical path between the image sensor and the interior surface, wherein the filter transmits the infrared light and attenuates visible light; and
  wherein the field of view of the camera is greater than 90 degrees.

8. The system of claim 3, wherein the image sensor utilizes a global shutter to obtain an exposure during an exposure period; and
the first device further comprising a controller that operates the light source to illuminate the at least a portion of the field of view during the exposure period.

9. The system of claim 3, the hardware processor to further execute the computer-executable instructions to:
  determine the second set of images using one or more edge detection algorithms.

10. The system of claim 3, the hardware processor to further execute the computer-executable instructions to:
  determine the second set of images using one or more feature detection algorithms to detect features having a minimum size.

11. The system of claim 3, wherein:
the first distance is indicative of a distance from a first edge to a second edge of the first blood vessel at the first time;
the second distance is indicative of a distance from a third edge to a fourth edge of the second blood vessel at the first time;
the third distance is indicative of a distance from the first edge to the second edge of the first blood vessel at the second time; and
the fourth distance is indicative of a distance from the third edge to the fourth edge of the second blood vessel at the second time; and
the hardware processor further configured to execute the computer-executable instructions to:
  determine that the first distance is greater than the second distance; and
  determine that the third distance is greater than the fourth distance.

12. The system of claim 3, the hardware processor to further execute the computer-executable instructions to:
  determine a first color value associated with the first blood vessel, wherein the first color value is based on a luminance value or a chrominance value provided by the camera;
  determine a second color value associated with the second blood vessel; and
  determine that the first color value is greater than the second color value.

13. The system of claim 3, the hardware processor to further execute the computer-executable instructions to:
  determine, using the first distance or the second distance, one or more of a systolic blood pressure value or a diastolic blood pressure value.

14. The system of claim 3, the hardware processor to further execute the computer-executable instructions to:
  acquire, via the communication interface, first data obtained by a sphygmomanometer, the first data indicative of a systolic blood pressure value and a diastolic blood pressure value at one or more times during a first interval of time;
  determine correspondence data specific to the user, based on the first data and distance values associated with the first and second blood vessels; and determine, based on the first distance, the second distance, and the correspondence data, data indicative of blood pressure of the user.

15. The system of claim 3, the first device further comprising:
at least one sensor to generate sensor data, wherein the at least one sensor comprises one or more of:
an accelerometer,
a gyroscope
a thermometer,
a glucose sensor,
an oximeter, or
a pulse sensor;
a second memory storing second computer-executable instructions; and
a second hardware processor, wherein the second hardware processor is configured to execute the second computer-executable instructions to:
determine that one or more values of the sensor data exceed a threshold value; and
operate the camera and the light source to generate the second set of images.

16. A method comprising:
acquiring a first image at a first time with an infrared camera within a band of a wearable device, wherein the first time corresponds to a first pressure;
determining that the first image depicts a first blood vessel and a second blood vessel;
determining, using the first image, a first distance between edges of the first blood vessel;
determining, using the first image, a second distance between edges of the second blood vessel;
acquiring a second image at a second time with the infrared camera, wherein the second time corresponds to a second pressure, and wherein the second pressure is greater than the first pressure;
determining that the second image depicts the first blood vessel and the second blood vessel;
determining, using the second image, a third distance between the edges of the first blood vessel;
determining, using the second image, a fourth distance between the edges of the second blood vessel;
determining a first relative change in distance of the first blood vessel from the first time to the second time based on the first distance and the third distance;
determining a second relative change in distance of the second blood vessel from the first time to the second time based on the second distance and the fourth distance;
determining the first relative change in distance of the first blood vessel is less than the second relative change in distance of the second blood vessel; and
determining that the first blood vessel is a vein based on the first relative change in distance of the first blood vessel being less than the second relative change in distance of the second blood vessel.

17. The method of claim 16, further comprising one or more of:
determining a percentage change in diameter from a minimum diameter to a maximum diameter of the first blood vessel or the second blood vessel, or
determining a ratio of a first diameter of the first blood vessel to a second diameter of the second blood vessel.

18. The method of claim 16, wherein:
the first distance is indicative of a distance from a first edge to a second edge of the first blood vessel at the first time;
the second distance is indicative of a distance from a third edge to a fourth edge of the second blood vessel at the first time;
the third distance is indicative of a distance from the first edge to the second edge of the first blood vessel at the second time; and
the fourth distance is indicative of a distance from the third edge to the fourth edge of the second blood vessel at the second time; and
the method further comprising:
determining the first distance is less than the second distance; and
determining the third distance is less than the fourth distance.

19. The method of claim 16, further comprising:
accessing blood pressure data, obtained from a sphygmomanometer, the blood pressure data derived from a set of images obtained at one or more different times, wherein the blood pressure data is indicative of a systolic blood pressure value and a diastolic blood pressure value;
determining a correspondence between the blood pressure data and distance values associated with the first and second blood vessels; and
determining, based on the correspondence, the first distance, and the second distance, data indicative of blood pressure.

20. The method of claim 16, further comprising:
determining, using the first distance or the second distance, one or more of a systolic blood pressure value or a diastolic blood pressure value.

21. The method of claim 16, wherein the determining that the first image depicts the first blood vessel and the second blood vessel comprises using one or more feature detection algorithms to detect features having a minimum size.

* * * * *